United States Patent [19]

Bambeck

[11] Patent Number: 5,589,104
[45] Date of Patent: Dec. 31, 1996

[54] ELECTROPHORESIS SEPARATION GEL AND A METHOD FOR PREPARING AN ELECTROPHORESIS SEPARATION GEL

[76] Inventor: Gregory S. Bambeck, 1890 Georgetown Rd., Hudson, Ohio 44236

[21] Appl. No.: 177,271

[22] Filed: Dec. 30, 1993

[51] Int. Cl.⁶ .............................. B01J 13/00; C25B 1/00
[52] U.S. Cl. ........................................ 252/315.1; 204/469
[58] Field of Search ........................... 252/315.01, 315.1; 204/182.8

[56] References Cited

U.S. PATENT DOCUMENTS

| | | | |
|---|---|---|---|
| 4,975,174 | 12/1990 | Bambeck et al. | 204/182.8 |
| 5,089,103 | 2/1992 | Swedberg | 204/182.8 |
| 5,387,325 | 2/1995 | Opplt | 252/315.1 |

*Primary Examiner*—Shean C. Wu
*Attorney, Agent, or Firm*—Benesch, Friedlander, Coplan & Aronoff

[57] ABSTRACT

A gel for use in an electrophoresis separation includes a plurality of gradients within the gel. Each gradient includes a polyacrylamide matrix and a buffer, wherein the polyacrylamide of one gradient has a different and preselected chain length as compared to at least one other gradient. The polyacrylamide matrix is a bi-functionally cross-linked acrylamide; and the buffer has a buffering capacity pH of from about 7.5 to about 9.5. A method according to the invention includes polymerizing the polyacrylamide matrix while monitoring polymer chain length and forming an electrophoresis gel therewith.

8 Claims, 1 Drawing Sheet

ELECTROPHORESIS SEPARATION GEL AND A METHOD FOR PREPARING AN ELECTROPHORESIS SEPARATION GEL

TECHNICAL FIELD

This invention relates to electrophoresis gel separations. More particularly, the invention relates to gradient gels useful in such separations. Specifically, the invention relates to a gel for use in such a separation, wherein the gel has gradients based upon the chain length of the gel polymer, the invention having particular application to the separation of lipoprotein subfractions.

BACKGROUND OF THE INVENTION

Electrophoresis involves the separation of charged macromolecular species in a carrier medium in an electric field. This involves the migration of charged molecular species through a porous gel under an applied electric field. Commonly used gels include polyacrylamides, typically crosslinked with a small amount of bis-acrylamide, and other similar gels.

Electrophoresis gels are often held in place by a cassette during use. Examples of gel electrophoresis devices are shown in U.S. Pat. Nos. 4,909,918 and 4,975,174 which patents are hereby incorporated by reference in their entirety.

One useful application of electrophoresis gel separation technology has been in the area of lipoprotein separations. As is known, cardiovascular disease is the leading cause of death in the developed world, accounting either directly or indirectly, for half of all deaths and consuming the largest single portion of health care costs. It is also generally known that cardiovascular disease is influenced at least indirectly, by the lipoprotein levels within the blood.

With this understanding in mind, there has been much effort expended in the area of lipoprotein separation. The early advancements in lipoprotein separations were performed by density gradient ultracentrifugation and the lipoproteins were found to consist of chylomicra, very low density lipoproteins (VLDL), intermediate density lipoproteins (IDL), low density lipoproteins (LDL), and high density lipoproteins (HDL). These subfractions were verified by for example, cellulose acetate and acrylamide electrophoresis, with agarose and acrylamide demonstrating that there was a precise inverse order between lipoprotein density and molecular size.

It has also been found that abnormally elevated LDL blood levels correlate with elevated cardiovascular disease risk. It is has been conversely found that elevated HDL levels correlate with increased cardiovascular health. More importantly, LDL and HDL are inversely co-dependant, and recent transgenic and "knock out" protocols have demonstrated a causal link in the co-dependency.

Improvements in centrifugation, the use of antibodies and improvements in electrophoresis led to further subfraction and functional analysis of the chylomicra, VLDL, LDL and HDL families of lipoproteins. The LDL family (LDLF) was found to contain four variations by centrifugation and seven variations by electrophoresis. In general, heavy LDLs are suggested as being strongly related to elevated cardiovascular disease risk.

Similarly, the HDL lipoprotein subfractions fall under three major classes, known as $HDL_1$, $HDL_2$, and $HDL_3$; with $HDL_1$ being the largest and least dense, $HDL_2$ being intermediate and $HDL_3$ being the smallest and most dense. The $HDL_1$ group has been further divided into $HDL_{1a}$, $HDL_{1b}$ and $HDL_{1c}$. The $HDL_1$ group is the only HDL group know to deliver lipids to tissues and the liver via protein receptor systems. The other HDL families are powerful lipid scavengers with $HDL_2$ being more efficient than the $HDL_3$. There appears to be a very strong correlation between $HDL_2$ and $HDL_3$ levels in cardiovascular disease risk. All of the HDLs can be collectively referred to as the HDL family (HDLF).

All of the lipoprotein subfractions appear to be regulated by discrete, large mass transfers, and an ability to monitor the subfraction quantities is critical to obtaining a precise understanding of the system, and subsequently, accurate diagnosis.

With the advent of acrylamide gel electrophoresis, it was possible to achieve separations which could match the resolutions of ultracentrifugation techniques. Quantitative equivalency to ultra centrifugation was established. With the introduction of gradient gels, based upon the concentration of the polyacrylamide within the various gradients, it was possible to surpass the resolving power of ultracentrifugation in the separation of both LDL subfractions and HDL subfractions.

There are at least two problems that occur with the use of high resolution gradient gels. First, heretofore known gels separate macromolecules on the basis of size and charge. If charge is a constant portion of molecular size in a dispersed macromolecular population, small molecules are separated predominantly by charge while large molecules closer to the pore size exclusion limit of the gel, are separated primarily on the basis of size. In a gradient gel, higher resolution is achieved as molecules are progressively separated on the basis of mass as the run time continues, regardless of charge differences. Ultimately, molecular mobility is halted as the macromolecules achieve their pore size exclusion limits. To reach pore size exclusion limits, or equilibrium, very long electrophoresis run times are necessary. If the macromolecules are very soluble, very high resolution can be achieved in short, nonequalibrium run times. If the macromolecules are insoluble, they cannot be electrophoresed at all. In standard, non-denaturing electrophoresis buffers of common use, HDLs are very soluble, LDLs are moderately soluble and VLDLs and IDLs are moderately to very insoluble.

A need exists therefore for an electrophoresis system which can simultaneously monitor the normal and abnormal amounts, types and compositions of lipoproteins, in a timely manner.

SUMMARY OF INVENTION

It is therefore, an object of the present invention to provide a gel useful for electrophoresis separations.

It is another object of the present invention to provide a gel as above which is useful for separating LDL fractions and subfractions in a timely manner.

It is yet another object of the present invention to provide a method of preparing a gradient gel for use in an electrophoresis separation.

At least one or more of the foregoing objects, together with the advantages thereof over the known art relating to electrophoresis gels, which shall become apparent from the specification which follows, are accomplished by the invention as hereinafter described and claimed.

In general the present invention provides a gel for use in an electrophoresis separation, which comprises a plurality of gradients within the gel. Each gradient comprises a polyacrylamide matrix and a buffer; wherein the polyacrylamide of one gradient has a different and preselected chain length as compared to at least one other gradient. The polyacrylamide matrix is a bi-functionally cross-linked acrylamide; and the buffer has a buffering capacity pH of from about 7.5 to about 9.5.

There is also provided according to the invention a method of preparing a gradient gel for use in an electrophoresis separation, which comprises the steps of polymerizing at a temperature below about 17 C., an acrylamide monomer to form a polymer; monitoring the chain length of the growing polymer, and removing a portion of the polymer at least two different chain lengths, to form a first polymer portion and a second polymer portion; separately mixing each first and second polymer portions with a buffer to form respectively, a first gradient gel and a second gradient gel; and, placing the first and second gradient gels into an electrophoresis gel cassette. The polyacrylamide matrix is a bi-functionally cross-linked acrylamide; and the buffer has a buffering capacity pH of from about 7.5 to about 9.5.

PREFERRED EMBODIMENT FOR CARRYING OUT THE INVENTION

Figure 1:
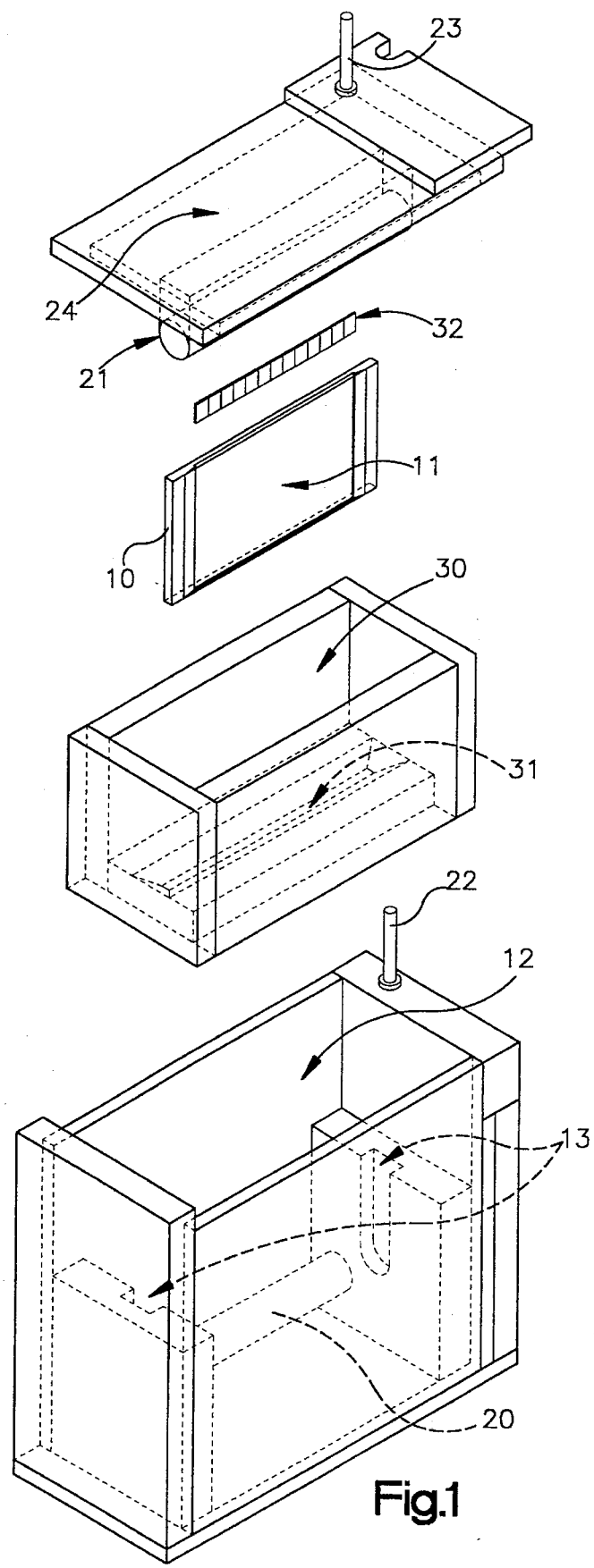
FIG. 1 is an exploded perspective view of a gel cassette apparatus useful in the practice of the present invention having a gradient gel therein according to the concepts of the present invention.

According to the present invention, a gel is provided which is useful in electrophoresis separations. The gel according to the invention is provided with at least two and preferably a plurality predetermined gradients therein, as will be more fully discussed hereinbelow.

Gels according to the present invention can be used in any electrophoresis device, such as those disclosed in U.S. Pat. Nos. 4,975,174 and 4,909,918 incorporated by reference hereinabove. Such devices often employ a cassette such as cassette 10, into which the gel is placed. The gel according to the invention is generally designated by the number 11 on the attached drawings.

Cassette 10 can then be suspended in a tank 12 such as by use of cassette guide rails 13 into which cassette 10 is received. Tank 12 is also provide with a pair of electrodes 20 and 21 such as by jacks 22 and 23 respectively. Electrode 21 and jack 23 may be positioned in a lid or cover set for tank 12. Normally, electrode 20 which is positioned at the bottom of tank 12, is an anode. In accordance with conventional electrophoresis separations, an upper tank 30 may also be employed, having a gasketed slot 31 therein, to receive cassette 10. A comb 32 may also be employed in a conventional manner.

Electrodes 20 and 21 are attached to an electric current (not shown) in a manner conventional for electrophoresis use. The material to be separated is introduced at the top of cassette 10, and the electrophoresis separation is allowed to proceed.

Preferably, the gel according to the invention is a bi-functionally cross-linked acrylamide or the like, in acrylic, allylic or vinyl form. For ease of this discussion, these polymers will be collectively referred to as the "gel polymer" unless the specific polymer is otherwise specifically stated. The chain length of the gel polymer is variably preselected, as will be more fully discussed hereinbelow. Similarly, the cross-linker preferably consists of a bifunctional acrylic, allylic, vinyl or mixed function allylic or vinyl form which comprises between about 1 and about 7 percent by weight of the total polymer present.

Preferably, the gels according to the present invention also include a buffer. While any buffering compound is within the scope of the invention, a preferred class of buffers include amino compounds which will yield a buffering capacity pH of between about 7.5 and 9.5. Such compounds include trishydroxyaminomethane (TRIS, THAM), ethylamine (EA), diethylamine (DEA), ethanolamine (EOA), (3-[cyclohexylamino]-2-hydroxy-1-propane sulfonic acid (CAPSO), (2-[N-cyclohexylamino]ethane sulfonic acid (CHES), (3-[1, 1-dimethyl-2-hydroxy ethyl)amino]-2-hydroxypropanesulfonic acid)(AMPSO), (N,N-bis[2-hydroxyethyl)glycine (BICINE), (3-[N,N-bis(2 hydroxyethyl)amino]-2-hydroxy propane sulfonic acid) (DIPSO), (N-[2-hydroxyethyl]piperazine-$N^1$-[2-ethanesulfonic acid (HEPES), (N,N-bis[2-hydroxyethyl]glycine) (BICINE), triethano-lamine (TEA), (N-tris[hydroxymethyl]methyl glycine (TRICINE), (N-tris [hydroxymethyl]-3-aminopropane sulfonic acid) (TAPS), (N-[2hydroxyethyl]piperazine-$N^1$[3-propane sulfonic acid] (EPPS), (N-[2-hydroxyethyl]piperazine-$N^1$-[2-hydroxy propane sulfonic acid] (HEPPSO), (piperazine-N,$N^1$-bis[hydroxy propane sulfonic acid] (POPSO), and the like. The buffer is mixed in water in concentrated form. The buffer concentrate is then co-diluted with polymer dissolved in water concentrate, and the mixture is polymerized into gel with the addition of conventional gel polymerization catalysts in conventional amounts.

As stated hereinabove, the gel such as gel 11 placed within cassette 10 includes a number of different gradients. Each of the various gradients can be defined by a function selected from $f(x)=Kx+C$ for linear gradients, $f(x)=Kx^y+C$ for logarithmic gradients, $f(x)=[K(x_1)+C_1]+[K(x_2)+C_2]$ for bipolar gradients, and combinations thereof, wherein:

f(x) is the volumetric cassette distance from gel gradient origin to gel gradient termination;

K is a gel percentage proportionality constant;

x is gel concentration;

y is a preselected logarithmic function; and,

C is the concentration of the gel at the origin of said gradient.

It has been unexpectedly found that during polymerization of the gel polymer, at temperatures below about 17 C., catalytic control of initiation and the rate of chain length elongation become differentially controllable. Thus, polymer chain length (PCL) control is established. By providing gradient gels based upon preselected PCLs, the resolving power of such gels when used for electrophoresis operations more than doubles when compared to non-gradient gels for macromolecules less than 2 million Daltons in mass.

It is believed that the rate of mobility and diffusional band spreading of sample macromolecules is controlled by the frictional coefficient, which in turn is controlled by pore size. The pore size in gels is controlled primarily by gel concentration and amount of cross-linking. In a biological sample, all macromolecules begin their migration at the low percentage end of the gradient gel and move progressively into the smaller pores toward the high concentration end of the gel. The smaller molecules end up in the high friction small pores, while the large molecules end up in the low friction large pores.

The gel polymer buffer preferably provides an acidic ion while the running buffer provides an alkaline ion. As discussed hereinabove, a large number of alkaline countercurrent ions and acidic counterions were considered for their effects on lipoprotein electrophoretic resolution. Target properties included optimum buffering pH in the presence of the counterion, mass related molecular activity, optimal ionic strength and lipoprotein solubilization vis a' vis gel matrix and lipoprotein interaction. In all cases, the ionic strength of the alkaline ion was used to establish the gel buffer, running buffer and prestain buffer molarity, while pH was established by titration with the acidic counterion. A molarity of 0.09M in alkaline ion was established as a 1× strength, and all subsequent experiments were described as using multiples or fractions of this molarity.

Alkaline countercurrent ions travel in the opposite direction of the lipoproteins during electrophoresis and are not relevant to the lipoprotein separation process, in terms of their size, hydrophobicity and hydrophilicity, as is the case with the acidic counterion, which is the primary carrier ion.

Acidic counterions must be of an intermediate hydrophilicity to hydrophobicity, as these are the principal lipoprotein carrier ions, and they must not dissolve or denature, by dispersion, the native mass of the lipoprotein structure; nor should they be so hydrophilic as to precipitate the lipoproteins or cause them to be adsorbed to the gel matrix. In general, small hydrophilic ions cause LDLF precipitation, large hydrophilic ions cause LDLF adsorption, small hydrophobic ions cause LDLF dissolution and large hydrophobic ions cause LDLF dispersion. Non ionic hydrophobes integrate into the particle, which is the basis for prestaining. Monofunctional acidic ions with a short two to six carbon, hydrophobic tail and bifunctionally acidic ions seem to protect lipids from the matrix surface with their negative charges, which causes the negatively charged lipoprotein to be electrostatically repelled from the matrix surface. The second negative counterion or the short hydrophobic tail, which is the second functional component of the anionic counterion, permit the lipoprotein to utilize low energy hydrophobic interactions, and to slip past the matrix in the absence of electrostatic and Van Der Wals friction. Thus, the decreasing pore size of the matrix operates purely as a mechanical frictional barrier in the absence of precipitation inducing electrostatic adsorption. Pre-electrophoresis helps to prime the matrix for the gentle entry of prestained lipoproteins into the gel matrix.

Within these constraints, any carbon backbone structure, containing one or more single or double carbon-carbon bonds and containing one or more acidic functional groups, such as carboxylic, sulfonic or phosphonic groups, is a likely counterion candidate, but it should be closely matched to the polymer matrix used. As stated hereinabove, typical polymer matrixes can include any gel forming acrylic, allylic or vinyl monomer with any number of modifying functional groups, in combination with a bifunctional cross linker containing any of the aforementioned monomeric properties, so as to form a polymer or mixed polymer gel with controllable pore size. The monomers and bifunctional cross linkers may be selected from a list including but not excluded to acrylic acid, acrylamide, allylcarboxyl compounds, allyl alcohol, allyl polyol or any mixed function acrylic containing carboxy, hydroxy or amide groups in any combination with a cross linker selected from for example, $N,N^1$ methylene-bis-acrylamide, $N,N^1$ methylene-bis-acryloyl cystamine, diacryloyl piperazine and derivatives, acrylaid, diallyl ditartarimide and others, with the cross-linker comprising from about 1 to about 7 percent by weight of the total polymer present, and polymerized in the presence of ultraviolet light, electron beams, microwaves or chemical free radical donators, such as ammonium peroxy disulfate, riboflavin 5' monophosphate, and others, and with or without catalytic modifiers such as tetraethylenemethylenediamine (TEMED). Other combinations within the framework of the objectives of the invention, described herein, can be envisioned.

The water solubility of the aforementioned acidic counterions can be modified with hydroxyl groups, amines, imines, alkanes, alkenes, aromatic rings, sulfonates phosphonates, pyridines, purines, pyrimidines or other known functional groups so that native lipoprotein integrity is preserved and gel matrix interactions are reduced in such a fashion so as to maximize the electrophoretic separation of the lipoprotein subfractions. A list of better candidates may be selected from for example, acetate, proprionate, butyrate, caproate, valerate, heptanoate, octanoate, taurine citrate, glutamate, aspartate, maleate, fumarate, succinate, glucaronate, lactate, laurate, hydroxybutyrate, glycolate, alkanoates with mono or polyhydroxyl groups, disaccharidic acids, sugar carboxylates, nucleic acids, phosphorurines or pyrimidines, sulfonopurines or pyrimidines, carboxy esters, phospho and/or phosphono esters, amino and hydroxy mixed function esters, alkyl or alkenyl phosphonates or sulfonates, phospho or sulfono or carboxy purines or pyrimidines, amino sugar or ester sugar acids, benzoates, mixed function benzoates, dipeptide acids, and the like.

The use of acidic range ampholytes as a carrier polybuffer is also within the scope of the invention. Ampholyte species are employed in a narrow acidic pH range that insures lipoprotein mobility in the gel, and can also affect separation by taking advantage of the focusing effect superimposed on the pore size exclusion effect of the gel gradient.

An ideal prestain reagent system is one in which a proven lipoprotein or lipid stain, such as 1-phenylazo-2-naphthol (sudan I), sudan II, sudan III, sudan IV, sudan black B, sudan red B, sudan red 7B, oil red O, oil red EGN, oil blue M, Oil blue N and their derivatives; wherein the reagent is dissolved in a solvent selected from gel buffer or other buffers, ethylene glycol, ethylene glycol monomethyl ether, ethylene glycol monoethyl ether, glycerol, trioses, tetroses, pentoses or other sugars or their derivatives and mixtures thereof. The reagent is solubilized in a buffer reagent system that is matched to the running and gel buffers, and stains the lipoproteins without denaturing the lipoproteins or leaving background stain in the gel. A preferred functional prestain systems is solubilized in 0.2× to 1× gel buffer in a pH range from 8.0–9.0 and solubilized in 85–96% ethylene glycol, ethylene glycol monomethyl ether, ethylene glycol monoethyl ether, glycerol and other methylene and ethylene substituted polyols or combination thereof, with the stain ranging from 0.02% to 0.5%, solubilized at 60° C. to 80° C. and filtered after cooling to room temperature.

The prestain is mixed with a sample to be resolved, such as a serum sample, wherein the dissolved stain interlacates between the hydrophobic lipid tails and the psuedo-phenanthrene ring plates of cholesterol, rendering the lipoproteins visible during electrophoresis. Similarly, the samples can be run as raw serum and the gel post-stained with the same stain to yield a more intense and quantitative staining of the lipoprotein subfractions.

General Experimental

In order to demonstrate the effectiveness of the present invention in providing for electrophoretic separation of lipoprotein subfractions, a number of experimental examples were conducted as will be described hereinbelow.

From the results of Example 1, bifocal or pseudotrifocal gradients were produced by mathematical design, in an attempt to maximize the separation of all LDLF and HDLF subfractions, simultaneously. Optimum buffer, ionic strength, pH continuity, stain system and gradient format were chosen from this set, so as to arrive at the maximum resolution lipoprotein subfractionation gel obtainable from this experimental design rationale. The particulars of these experiments are provided in Example 2.

In the following examples, a particular nomenclature is employed for describing bifocal or bilinear gradient gels. The length of the gel is considered as 100% of the gel length. Because there are two fused linear gradients in the gel, they are described in terms of the total distance of the gradient that each occupies. The notation A/B is used to describe this relationship. "A" refers to the percentage of the total distance occupied by the low percentage gradient at the sample application end of the gel to the fused region with the second gradient. "B" in turn supplies the same reference to the second gradient. To describe the percentage of gel in each gradient, the form C-D/E-F (C to D then E to F) is used. To describe the mathematical style of gradient, the letter "k" can be used to describe single percentage non gradients, the letter "a" can be used to describe linear (arithmetic) gradients and the letter "l" can be used to describe logarithmic gradients. Thus, the notation 40/60 1–7,a/9–20,1 would represent a bifocal gel in which the top 40% of the gel is occupied by a 1–7% linear (arithmetic) gradient gel, fused to the bottom 60% of the gel, which is composed of a 9–20% logarithmic gel gradient. Because all bifocal gels used herein are arithmetic (linear) gel gradients, the lower case letter designation has been dispensed with. A 40/60 1–7/ 9–20 refers to a gel the same as the one described above, but with two fused linear gradients. The fused region of the gel is actually a gradient of its own, which represents about a 5–7% region of gel length containing a sigmoidal gradient increase from the high percentage terminus of the low percentage gradient, to the low percentage end of the high percentage gradient, as defined by the Law of Diffusion, where $dX/dC = D \log t$, where x is the diffusion distance, C is the concentration, D is the diffusion coefficient (which incorporates molecular size, frictional coefficient, temperature, viscosity) and t is time. Because there are two concentrations in this case, there are two logarithmic functions diffusing into each other, creating a sigmoid gradient. Thus, bifocal gels may be thought of as being "trifocal" in nature.

In Example 3, electrical and gel cooling parameters were tested on the optimized gels from Example 2. Pulsed electricity from 0–30,000 HZ was tested at various voltages ranging from 50 V to 300 V with and without cooling. The electrophoresis device was fitted with inlet and outlet ports which were attached to silicone tubing running through cooling coils into a bath and through peristaltic pumps for cooling on high voltage electrophoresis experiments. Since different buffers were used in the top and bottom tanks, separate cooling systems were employed for each tank.

In Example 4, optimized buffers, stains, and electrical running conditions were applied to a set of gradient gels for VLDLF only and HDLF only subfractionation. The objective was to optimize gels for a specific class of lipoprotein subfractions so that continued research could be performed on elucidation of rare genotypic and phenotypic variations. These gels could also be used for elucidation of the fine structure of a diagnosed abnormality localized to a specific lipoprotein family during routine screening with the total lipoprotein subfraction gel.

Throughout each experiment, over 600 gels and 7000 samples of human serum samples were run. Quantitative densitometry was performed on selected gels to demonstrate the progressive improvements made by the rational example design sequence described hereinbelow.

EXAMPLE 1

Logarithmic Gel Parameters

The buffers in the logarithmic gradient gels and running buffer were selected from a group composed of either 1×, 2×, 3×, 4× or 6× tris acetate, tris proprionate, tris butyrate, tris valerate, tris caproate, tris succinate, tris gluconate or tris adipate. The buffers were prepared from concentrates at 8× at pH 7.7, 8.0, 8.3 or 9.0. The same buffers, as listed above, were prepared with 0.1×, 0.4×, 0.8× or 1.2× at a stain concentration of 0.05%, 0.01% or 0.5% in 95% ethylene glycol, ethelene glycol monoethyl ether or glycerol. From the pre-example experimentation, it was demonstrated that the anionic counterion in the gel and stain should be the same, for highest resolution results.

All 2–16% and 4–30% gradient gels were composed of acrylamide and $N,N^1$ methylene bis acrylamide in which the cross-linker was either 3% or 5% of the total acrylamide copolymer concentration. The 2–16% gels used were PCL controlled logarithmic gradients of the form $f(x)=y^{1.8}+2$ while 4–30% gels used were PCL controlled logarithmic gradients of the form $f(x)=y^{1.8}+4$. The power function 1.8 was chosen because gel pore size, at least from about 7–33% changes throughout the length of the gel as a linear function of macromolecular weight. In linear gradient gels, the relationship is semi logarithmic. Only about one fourth of all of the possible combinations were tested because data trends began to eliminate poor electrophoretic resolving power combinations from the logical intent of the matrix design.

LDLF subfractions were resolved best on 2–16% gels while HDLFs all ran off the gel before the LDLFs were resolved. On 4–30% gels, all LDLF subfractions were crowded into a single band near the top of the gel while HDLF subfractions were highly resolved about two thirds of the way down the gel. Anions more hydrophobic than butyrate caused VLDL and IDL dispersion or solubilization in the absence of preelectrophoresis, while they yielded superior results with HDLF subfractions as long as they were not more hydrophobic than hexanoate. Gel pretreatment with laurate increased resolution of all subfractions.

Buffers used in gels or used as running buffers that were more hydrophilic than acetate, precipitated VLDL, IDL and LDL to some degree. This clearly demonstrates why standard tris phosphate, tris-HCL, tris glycine, tris borate and tris citrate systems fail to achieve high resolution in less than equilibrium run times.

The fastest running gels were 1× and 2× in buffer, and also yielded the highest resolution separations. Bottom tank buffers with pH 8.0 at 1× or 2× concentration worked best in combination with top tank buffers of pH 9.0 and a concentration of 2× to 4×. The best buffers in gels and as running buffers were composed of tris propionate, tris butyrate, tris gluconate and tris adipate. This combination of buffers is intermediate in water solubility between the most hydrophilic and hydrophobic buffers used and a smooth continuum of the effects previously described, in a hydrophilicity to hydrophobicity sense, was unambiguously proven. Within this continuum, dianionic carrier ions demonstrated their lipoprotein protective effects.

As described, the best results utilized discontinuous pH and ionic strength buffer conditions in the top buffer tank, the gel and the bottom buffer tank. The buffers and stains finally selected could be used in virtually any combination and obtain fine resolution. However, certain buffers resulted in gels with longer shelf life. In the interests of efficiency, however, the gels run in Example 2 were selected from a far more narrow set of possibilities than could be selected from to achieve the same or similar results. In other words, the solutions chosen for Example 2 may not have been the absolute optimum, but they were from a highly optimized list, nevertheless. The independent variable of interest in Example 2 is gel gradient bifocality.

EXAMPLE 2

Bifocal Gel Parameters

In this example, all of the gel gradients were bifocal, with the lower percentage gradient primarily reflecting the concentration and steepness of the first third to half of a 2–16% logarithmic gel, and the higher percentage gradient designed to reflect the concentration and steepness of the last half to two thirds of a 4–30% logarithmic gel. Utilizing the nomenclature described previously, gel types tested were: 30/70 2-8/9-27; 40/60 2-7/8-27; 50/50 1-7/8-27; 40/60 1-6/7-27.

All top tank buffers were 2×–6× tris propionate, tris butyrate, tris adipate and tris gluconate, at pH of 9.0. The same buffers at pH 8.0 and 1×–2× were used in the bottom chamber. Sudan black B, which may or may not be the best stain, but appears to be one of the better ones, was used at 0.1% in 0.4× gel buffer. Gel buffers were all 1× or 2×, matched to the buffer/stain system and were run in every running buffer combination.

All gels demonstrated LDLF and HDLF subfractionation in short nonequilibrium run times. The advantage supplied by PCL controlled bifocality was equal to or superior to the best results obtained, for each group, on both of the 2–16% and 4–30% gels. In short, bifocal gels combined the best results obtained from two logarithmic systems, but did it in a single non-equilibrium run in a single gel. To my knowledge, this has never been accomplished prior to this example. In addition, it was achieved in a gel less than half the length and in one fourth the volt hours of each single style gel of the existing logarithmic system. Thus, the bifocal system is at least eight times more efficient than the two gel logarithmic gradient equilibrium system used today. The 50/50 1-7/8-27 gel yielded the best dynamic range and overall positioning of the data base.

EXAMPLE 3

Electrical Requirements

This example is used to establish the optimum electrical and cooling conditions for bifocal gels. The only style of bifocal gel run was the 50/50 1-7/8-27 gel. Gel voltage range was from 100 V to 300 V, with constant direct current or pulsed current up to 30,000 HZ. Because the system is discontinuous, top and bottom tank buffers were cooled separately. Since previous experiments had shown that optimal separations occur between 24° C. and 34° C., temperatures were kept in this range at all times. Gels were run with and without pre-electrophoresis. Buffers were chosen as described in Example 2.

To remain inside the temperature range, gels had to be cooled at voltages over 150 V. Gels at 200 V ran four times faster than gels at 100 V and gels at 300 V ran nine times faster than gels at 100 V, demonstrating that run time is inversely related to the square of the voltage. Serious loss in resolution begins to occur beyond 250 V. Preelectrophoresis achieves high resolution and preserves IDL and VLDL integrity better than no pre-electrophoresis. The highest resolution occurs between 120 and 180 volts at the higher frequency hertz range of pulsed voltage.

EXAMPLE 4

Special Function Gels

From the results of the first three examples, it was shown that the total lipoprotein, non-equilibrium, prestain subfractionation system could be utilized to design separate LDLF subfractionation and HDLF subfractionation gels with far superior resolution and efficiency than that of 2–16% logarithmic and 4–30% logarithmic gradient gels. A simple 1–8% PCL controlled linear gradient gel, run by the method developed herein, runs much faster and achieves much higher resolution on LDLF subfractions than a 2–16% logarithmic equilibrium or non-equilibrium gel, or on a bifocal gel. Similarly, a linear 6–24% PCL controlled gel runs much faster, and achieves higher resolution on HDL fractions than does a 4–30% logarithmic equilibrium or non-equilibrium gel, or on a bifocal gel.

All of the parametric advantages of Examples 1, 2, and 3 increase the resolution on both of these gel types. The optimum buffer systems on bifocal gels are also optimum on linear 1–8% gels, while the best HDLF subfraction resolution is achieved with slightly more non polar anionic buffers than those used with LDLF subfractionation gels.

Thus it has been shown that at least 15 lipoprotein subfractions, including at two forms of VLDL, one form of IDL, seven forms of LDL, one form of MDL and five forms of HDL can be separated on a bifocal or trifocal gradient acrylamide gel of appropriate buffer composition, ionic strength, pH and gel of appropriate design, as described herein.

Thus it should be evident that the device and methods of the present invention are highly effective in providing an electrophoresis gel. The invention is particularly suited for lipoprotein subfraction separations, but is not necessarily limited thereto. The device and method of the present invention can be used separately with other equipment, methods and the like.

Based upon the foregoing disclosure, it should now be apparent that the use of the gel described herein will carry out the objects set forth hereinabove. It is, therefore, to be understood that any variations evident fall within the scope of the claimed invention and thus, the selection of specific component elements can be determined without departing from the spirit of the invention herein disclosed and described. Thus, the scope of the invention shall include all modifications and variations that may fall within the scope of the attached claims.

What is claimed is:

1. A gel for use in an electrophoresis separation comprising:

a plurality of gradients within said gel;

each said gradient comprising a polyacrylamide matrix and a buffer;

wherein said polyacrylamide of one said gradient has a different and preselected chain length as compared to at least one other said gradient;

wherein said polyacrylamide matrix is a bi-functionally cross-linked acrylamide; and said buffer has a buffering capacity pH of from about 7.5 to about 9.5.

2. A gel, as set forth in claim 1, wherein said polyacrylamide matrix is selected from the group consisting of acrylic, allylic or vinyl based monomers in combination with a bifunctional cross-linker selected from of acrylic, allylic or vinyl based cross-linkers.

3. A gel, as set forth in claim 1, wherein the gel further comprises an alkaline cation selected from the group consisting of trishydroxyaminomethane; ethylamine; diethylamine; ethanolamine; (3-[cyclohexylamino]-2-hydroxy-1-propane sulfonic acid; (2-[N-cyclohexylamino]ethane sulfonic acid; (3-[1,1-dimethyl-2-hydroxy ethyl)amino]-2-hydroxypropanesulfonic acid); (N,N-bis[2-hydroxyethyl)glycine; (3-[N,N-bis(2-hydroxyethyl)amino]-2-hydroxy propane sulfonic acid); (N-[2-hydroxyethyl]piperazine-$N^1$-[2-ethanesulfonic acid; (N,N-bis[2-hydroxyethyl] glycine);triethano-lamine; (N-tris[hydroxymethyl]methyl glycine; (N-tris[hydroxymethyl]-3-aminopropane sulfonic acid); (N-[2hydroxyethyl]piperazine-$N^1$[3-propane sulfonic acid]; (N-[2-hydroxyethyl]piperazine-$N^1$-[2-hydroxy propane sulfonic acid]; and, (piperazine-N,$N^1$-bis[hydroxy propane sulfonic acid].

4. A gel, as set forth in claim 1, wherein said gel further comprises anionic counterion selected from the group consisting of acetate, propionate, butyrate, caproate, valerate, heptanoate, octanoate, taurine, citrate, glutamate, aspartate, maleate, fumarate, succinate, glucuronate, lactate, hydroxybutyrate, glycolate, laurate, alkanoates with mono or polyhydroxy groups, mixed alkanoic and alkenoic acids with or without mono or polyhydroxy groups, disaccharidic acids, sugar carboxylates, nucleic acids, phosphopurines or pyrimidines, sulfono purines or pyrimidines, carboxy esters, phospho or phosphono esters, amino or hydroxy mixed function esters, alkyl or alkenyl phosphonates, or sulfonates, phospho or sulfono purines, pyrimidines, indoles or their derivatives, amino ester sugar acids, benzoates, dipeptide or polypeptide acids, acid polymers of said above anions, and acidic ampholytes.

5. A gel, as set forth in claim 1, further comprising a lipoprotein staining reagent selected from the group consisting of sudan I, sudan II, sudan III, sudan IV, sudan black B, sudan red B, sudan red 7B, oil red O, oil red EGN, oil blue M, Oil blue N; wherein the reagent is dissolved in a solvent selected from said gel buffer, ethylene glycol, ethylene glycol monomethyl ether, ethylene glycol monoethyl ether, glycerol, trioses, tetroses, pentoses and mixtures thereof.

6. A gel, as set forth in claim 1, wherein the gel has at least two gradients each defined by a function selected from $f(x)=Kx+C$, $f(x)=Kx^y+C$, $f(x)=[K(x_1)+C_1]+[K(x_2)+C_2]$, and combinations thereof, where:

$f(x)$ is the volumetric cassette distance from gel gradient origin to gel gradient termination;

K is a gel percentage proportionality constant;

x is gel concentration;

y is a preselected logarithmic function; and,

C is the concentration of the gel at the origin of said gradient.

7. A method of preparing a gradient gel for use in an electrophoresis separation; comprising the steps of:

polymerizing at a temperature below about 17 C., an acrylamide monomer to form a polymer;

monitoring the chain length of the growing polymer, and removing a portion of said polymer at least two different chain lengths, to form a first polymer portion and a second polymer portion;

separately mixing each said first and second polymer portions with a buffer to form respectively, a first gradient gel and a second gradient gel; and, placing said first and second gradient gels into an electrophoresis gel cassette;

wherein said polyacrylamide matrix is a bi-functionally cross-linked acrylamide; and said buffer has a buffering capacity pH of from about 7.5 to about 9.5.

8. A gel for use in an electrophoresis separation, comprising the gel prepared according to the method of claim 7.

* * * * *